United States Patent
Müller

(10) Patent No.: US 7,099,430 B2
(45) Date of Patent: Aug. 29, 2006

(54) COMPUTED TOMOGRAPHY APPARATUS WITH A DETECTOR DIAPHRAGM HAVING A DIAPHRAGM ELEMENT MOVABLE LONGITUDINALLY OVER THE DETECTOR

(75) Inventor: Hans-Jürgen Müller, Pretzfeld (DE)

(73) Assignee: Siemens Aktiengesellschaft, Munich, DE (US)

( * ) Notice: Subject to any disclaimer, the term of this patent is extended or adjusted under 35 U.S.C. 154(b) by 0 days.

(21) Appl. No.: 11/074,449

(22) Filed: Mar. 8, 2005

(65) Prior Publication Data
US 2005/0201512 A1 Sep. 15, 2005

(30) Foreign Application Priority Data
Mar. 12, 2004 (DE) ............ 10 2004 012 243

(51) Int. Cl.
*G21K 1/12* (2006.01)
*G01B 15/02* (2006.01)
(52) U.S. Cl. .......................... 378/19; 378/4; 378/98.8
(58) Field of Classification Search ............ 378/4, 378/15, 19, 98.8, 145–160
See application file for complete search history.

(56) References Cited

U.S. PATENT DOCUMENTS

| | | | | |
|---|---|---|---|---|
| 2,696,634 A | * | 12/1954 | Kizaur | 264/277 |
| 4,490,835 A | * | 12/1984 | Wons | 378/146 |
| 5,233,193 A | * | 8/1993 | Arakawa | 250/580 |
| 6,173,033 B1 | * | 1/2001 | Klingenbeck-Regn et al. | 378/20 |
| 6,339,636 B1 | * | 1/2002 | Ogawa | 378/146 |

FOREIGN PATENT DOCUMENTS

DE    102 11 948    10/2003

\* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

A computed tomography apparatus has a gantry with at least one x-ray tube and at least one detector. The x-ray tube and the detector are executed such that they can rotate around a system axis (z-axis), and the detector exhibits a width B in the system axis direction and a longitudinal length L in the circumferential direction of the gantry. At least one movable detector diaphragm is arranged that is moved in front of the detector as needed and thus partially covers the detector. A movement device enables movement of the detector diaphragm over the detector in the longitudinal direction of the detector.

19 Claims, 3 Drawing Sheets

COMPUTED TOMOGRAPHY APPARATUS WITH A DETECTOR DIAPHRAGM HAVING A DIAPHRAGM ELEMENT MOVABLE LONGITUDINALLY OVER THE DETECTOR

BACKGROUND OF THE INVENTION

1. Field of the Invention

The present invention concerns a computed tomography apparatus of the type having a gantry with at least one x-ray tube and at least one detector, the x-ray tube and the detector being rotatable around a system axis (z-axis), and the detector exhibits a width B in the system axis direction and a length L in the circumferential direction, and furthermore a diaphragm with at least one movable element disposed in front of the detector and thus partially covers the detector as needed.

2. Description of the Prior Art

It is generally known that the resolution can be improved in an x-ray detector by a reduction of the size of the aperture which, among other things, describes the opening ratio or the power of an optical system, as described in German OS 102 11 948, for example. In this document, a diaphragm is described that has a movable element that at least partially covers the surface of the detector elements.

In modern x-ray computed tomography apparatuses, generally multi-row detectors are used that are arranged next to one another in the direction of the system axis (z-axis). Each detector row is formed by a number of detector elements in a direction perpendicular to the z-axis. To improve the resolution of these detectors, as needed a detector diaphragm can be attached in front of the detector that reduces the effective surfaces of the individual detector elements.

Newer developments in detectors exhibit an ever-greater width in the z-direction, which also requires a diaphragm that is wider in the z-direction. Since this detector diaphragm is moved over the detector only as needed, it must otherwise be disposed outside of the beam path in a standby position. This diaphragm is always moved, as is conventional, over the detector in the z-direction. This movement path requires a large amount of space in the z-direction. The gantry housing must accordingly also provide corresponding storage (stowage) space for the detector diaphragm, and is therefore construed correspondingly deep in the z-direction.

This design depth, however, causes a limitation of the collision diagram outline (i.e., the area in which a risk of collision exists), and thus a limitation with regard to the tilt capability of the gantry and with regard to the detector in general also arises. If one wants to obtain a sufficient tilt capability in spite of this larger design depth of the gantry housing in the z-direction, the radially closed examination space must be enlarged, which leads to unnecessarily large radii and therewith high construction costs.

SUMMARY OF THE INVENTION

An object of the present invention is to provide a computed tomography apparatus with a movable detector diaphragm, with a reduction of the design depth of the gantry housing along the z-axis, so tilting of the gantry with regard to the z-axis is less limited.

The inventor proceeds from the recognition that it is more advantageous to arrange the movable detector diaphragm such that it moves in the longitudinal direction of the detector. The necessary storage and movement space for the diaphragm thus can be mounted in the gantry housing in a space-saving manner, and the gantry housing can be shortened in the z-direction.

Thus in accordance with the invention a computed tomography apparatus has a gantry with at least one x-ray tube and at least one detector, wherein the at least one x-ray tube and the at least one detector are rotatable around the system axis, and the at least one detector exhibits a width B in the system axis direction and a longitudinal length L in the circumferential direction of the gantry, and at least one movable detector diaphragm is disposed to be moved in front of the detector as needed so as to partially cover the detector, and a movement device that enables movement of the detector diaphragm in the longitudinal direction of the detector.

The storage and movement space of the diaphragm, which in known computer tomography apparatuses was dependent on the diaphragm being movable parallel to the z-axis and also along the z-direction, can now be mounted in the circumferential direction with regard to the z-axis, and the gantry housing can be shortened with regard to the design depth in the z-direction. The possible tilt angle of the gantry is enlarged by this reduction. The diameter of the gantry can also be correspondingly reduced given the same tilt capability.

The movement of the diaphragm in front of the detector or away from the detector should be effected in an uncomplicated manner. This can be accomplished by a device that has at least one guide track or rail that supports the movement of the detector diaphragm. A faster and more friction-free movement course of the diaphragm is achieved. Two guide tracks, respectively on both sides of the diaphragm, can be used. The guide track can have roller elements, preferably ball bearings or roller bearings. The friction upon movement of the detector diaphragm thus can be decreased further.

As an alternative or enhancement to this, the detector diaphragm also (or instead) can be equipped with roller elements.

It is advantageous to fasten the detector diaphragm to at least one flexible pulling element. The force necessary for movement of the detector diaphragm thus can be produced in a particularly simple manner. Furthermore, the pulling element offers the possibility to apply the force at an advantageous location. An arrangement of the drive element directly at or near to the detector region and the covering detector diaphragm is thus possible only in a difficult manner due to the lack of space.

For example, a cable and/or a chain is suitable as a flexible pulling element. An additional guidance of the diaphragm can be supported by the flexibility of a cable and/or a chain in at least two spatial directions independent of one another. Due to the flexibility of the cable or chain, an adaptation of the diaphragm mechanism to the casing or wall of the gantry is possible.

The detector diaphragm can be moved manually. However, it is more comfortable and, for automation of the movement of the detector diaphragm, it is advantageous to apply at least one drive mechanism for the detector diaphragm that moves the detector diaphragm in front of and away from the detector. Such a drive mechanism, for example, can be an electrical step motor that is controlled by an encoder. An exact positioning of the diaphragm at the desired position in front of the detector thus is enabled. However, other motors, such as electromechanical, hydraulic or pneumatic motors, or adjustment elements such as piezo-adjustment elements are also suitable for this. The positioning of the detector diaphragm also can ensue by means of limit switches, for example.

The detector of the computed tomography apparatus can be a multi-row detector formed of a number of detector rows that each contain a number of detector elements. The resolution capability is thus optimized. The diaphragm should exhibit a division that approximately corresponds to the division of the multi-row detector. The aperture can be reduced by this diaphragm execution. The division of the diaphragm can be created by holes and/or slits that are introduced into the diaphragm material.

The detector diaphragm, which is composed of metal, should be executed such that it is flexible in at least the detector longitudinal direction. The flexibility can be achieved, for example, by adaptation of the material thickness, such that the detector diaphragm is approximately adapted or adaptable to the curvature of the surface of the detector.

Flexibility and thus adaptation of the detector diaphragm to different curvature radii also can be achieved by forming the detector diaphragm from a number of individual elements. For example, such individual elements can be connected with one another by hinge-like elements. If lead is used as detector material, which is not particularly flexible even at relatively thin material thicknesses and tends to break given small bending radii, sufficient mobility and adaptation to curvature radii can be achieved by the execution of the detector diaphragm from individual elements.

The individual diaphragm elements also can be pushed/pulled in succession in front of the detector. As an alternative to the individual diaphragm elements being connected by hinge elements, individual elements that are not connected with one another can be used in this embodiment. Each individual diaphragm element is positioned such that it can move in guide tracks, and that given contact, for example, the last individual element pushes the preceding individual element into the desired position. By using only individual detector elements, only individual regions of the detector can be covered, in a particularly simple manner.

Further advantages follow from the execution of the detector diaphragm from a number of individual elements. Thus, for example, a number of individual diaphragm elements that are respectively flexible can be layered (stacked) over one another. By stacking a number of individual diaphragm elements, the absorption behavior of the detector diaphragm can be adapted overall to different radiation strengths of the x-ray tube.

In another embodiment a storage volume is arranged in the gantry in the circumferential direction, within which storage volume the detector diaphragm is stowed immediately upon moving out of a position in front of the detector. The diaphragm can hereby be stowed in a space-saving manner.

DESCRIPTION OF THE PREFERRED EMBODIMENTS

Figure 1:
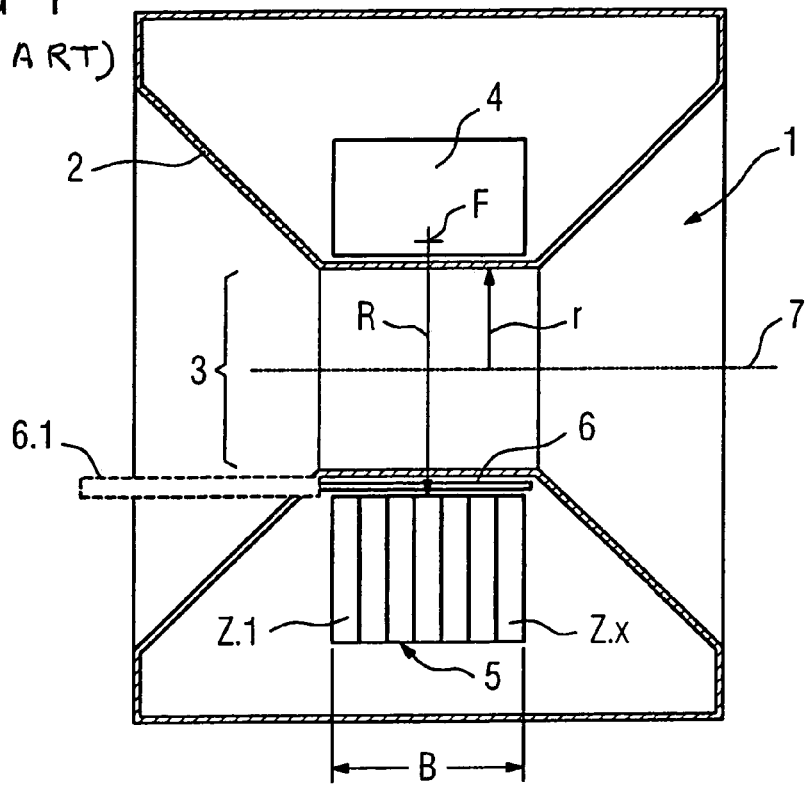
FIG. 1 is a section view parallel to the z-axis through a CT gantry.

In the following, the invention is described in detail using preferred exemplary embodiments with the following designations in Figures: 1: section 2 through the CT gantry, gantry casing 3, patient opening 4, x-ray tube 5, multi-row detector 6, diaphragm 6.1, standby position for the diaphragm 6.2, slit 6.3 in the diaphragm 6.1, diaphragm web 6.4, diaphragm with movement mechanism 6.5, arrow symbolizing the possible movement directions of the diaphragm 6.1, z-axis 8, roller element 9, chain 10, drive motor 11, guide element for diaphragm 12, bearing element F, focus Rf the x-ray tube R, curvature radius r of the surface of the detector, radius B of the patient opening B, detector width L, detector length Z.1–Z.x, detector rows S.1–S.x, detector elements 1 through x.

FIG. 1 shows a section view 1 parallel to the z-axis 7 through the center of a gantry of a computed tomography apparatus. For examination, a patient is moved into the gantry parallel to the z-axis and through the patient opening 3. The patient opening 3 (here round) exhibits a radius r. In this embodiment, the gantry has a funnel-shaped cross-section in the upper and lower region of FIG. 1, in that the casing 2 of the gantry conically tapers towards the gantry inner space. In FIG. 1, the x-ray tube 3 with the x-ray beam focus F is shown in the upper half of the gantry, opposite the multi-row detector 5. The distance of the curved detector surface from the focus F is designated with R. The multi-row detector 5 is formed of a number of detector rows Z.1 through Z.x proceeding in the z-direction and here extending over a detector width B. The x-ray tube 4 and the detector 5 can rotate around the z-axis 7.

In order to reduce the aperture of the detector 5 and to simultaneously increase the resolution, a diaphragm 6 is moved in front of the detector 5 as needed. If the diaphragm 6 is not necessary, this is stored in a standby position 6.1.

In FIG. 1, for explanation the standby position 6.1 as it was executed in known CTs is indicated dashed. The movement direction of the diaphragm 6 was oriented parallel to the z-axis 7. The gantry housing thus had to be constructed deep along the z-axis 7. The design depth of the gantry housing resulted due to the detector width B and the length of the park position 6.1. However, this high design depth of the gantry housing along the z-axis 7 negatively affects the possible tilt angle range of the gantry with regard to the patient bed. Moreover, the large design depth of the gantry housing parallel to the z-axis 7 also causes an enlargement of the "tunnel effect". Claustrophobic patients experience a long and nearly sealed examination region within the gantry as being uncomfortable. By foregoing the standby position 6.1 shown with a dashed line a compact design depth of a novel CT is enabled.

In order to attain such a compact design depth of the gantry housing with regard to the z-axis 7, in accordance with the invention the movable diaphragm 6 for the detector 5 is not mounted so that it can move parallel to the z-axis 7, but instead is mounted so as to move the diaphragm 6 over the detector 5 in the circumferential direction or longitudinal direction of the detector 5. Various embodiments and perspectives of such a movable diaphragm 6 are shown in FIGS. 2 through 7.

Figure 2:
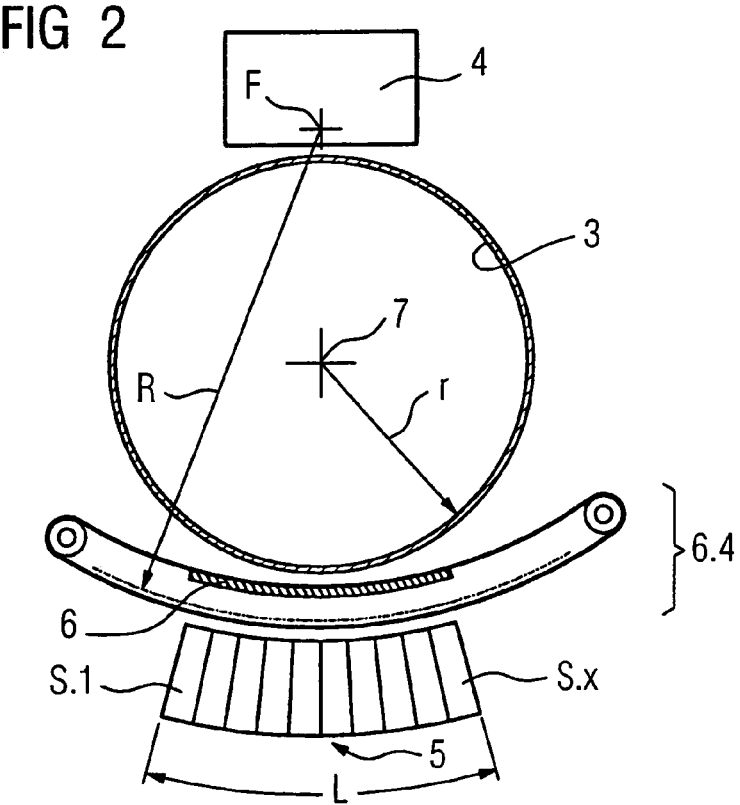
FIG. 2 is section view perpendicular to the z-axis of a CT gantry of a CT with a movable diaphragm in accordance with the invention.

FIG. 2 shows a sectional view perpendicular to the z-axis of a gantry of a CT with novel movable diaphragm 6.4. In this view, the patient opening 3 (here circular) with radius r is visible. Located in the upper region is the x-ray tube 4 whose x-ray beam exhibits a focus F, and opposite this is the detector 5 whose surface exhibits a curvature radius R. The curvature radius R corresponds to the distance from the focus F to the detector surface. In this embodiment of the diaphragm with the movement mechanism 6.4, the diaphragm with the movement mechanism 6.4 can be adapted to the radius R of the detector surface, and diaphragm 6 is shifted in the detector longitudinal direction, thus along L, and perpendicular to the z-axis that here lies perpendicular to the plane of the drawing.

Figure 3:
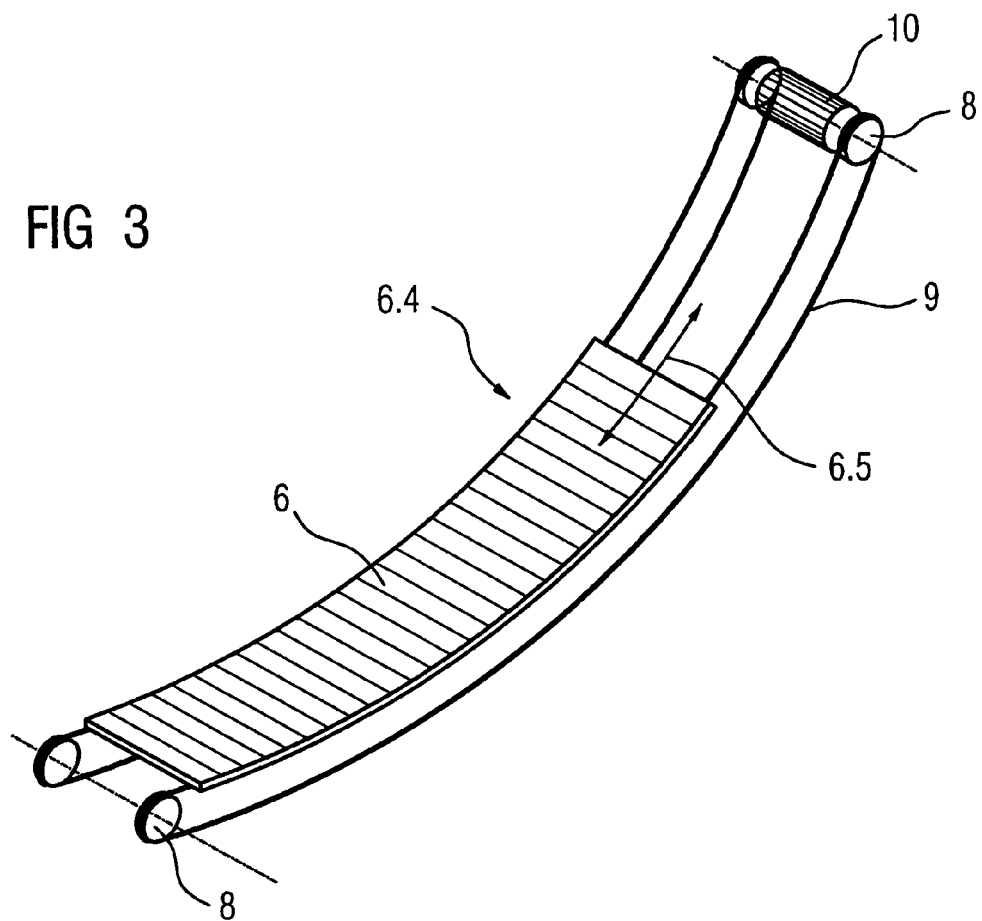
FIG. 3 is a perspective view of a movement mechanism with the diaphragm and drive motor in accordance with the invention.

FIG. 3 shows a perspective view of a diaphragm with a movement mechanism 6.4 that is driven (actuated) by a drive motor 10. In this embodiment, the movement mechanism is formed by two chains 9 that are entrained over two roller elements 8. The diaphragm 6 is fastened between these two chains 9. A drive motor 10, preferably an electromotor, is additionally mounted at the upper roller element 8. The movement directions of the diaphragm 6 are symbolized by the double arrow 6.5. If the diaphragm 6 is made, for example, from a metal plate only a few millimeters thick (preferably 1 to 2 mm), due to the material flexibility resulting in this range in most metals the radius of the patient opening r (or even smaller radii) can thus be circumscribed with the diaphragm 6.

Figure 4:
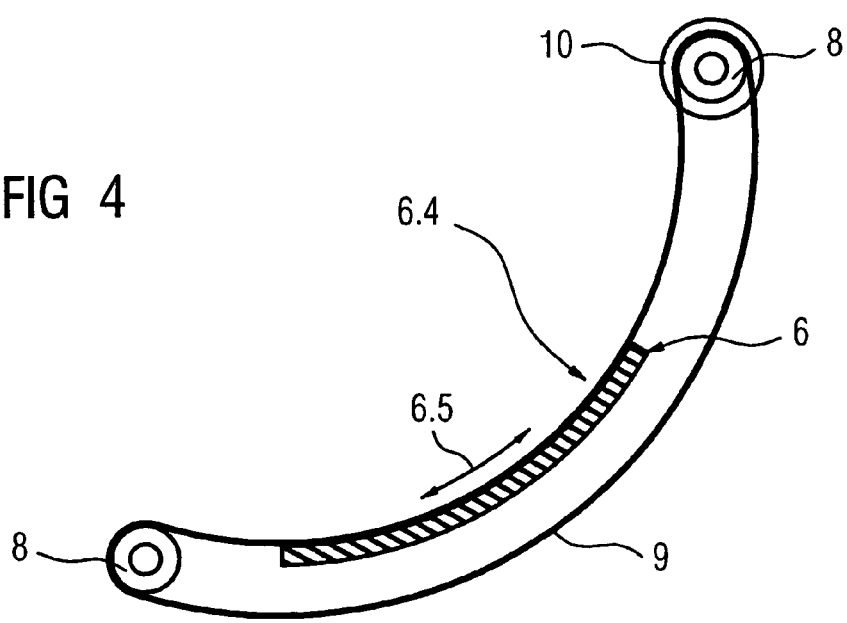
FIG. 4 is a side view of the movable diaphragm of FIG. 3.

The diaphragm is shown in FIG. 4 in a side view, with a movement mechanism 6.4 from FIG. 3. In this view, the nearly quarter-circular shape of the diaphragm 6 and a chain 9 is particularly easy to recognize. The curvature radius of this quarter-circle should approximately correspond to the radius R of the detector surface curvature, at least in the region of the detector surface. The movement mechanism can also be adapted to given curvature radii of the gantry outside of the detector surface. In order to be sufficiently movable along the curvature, the diaphragm 6 should be comprised of a flexible material or a material already preformed corresponding to the desired curvature radius.

Figure 5:
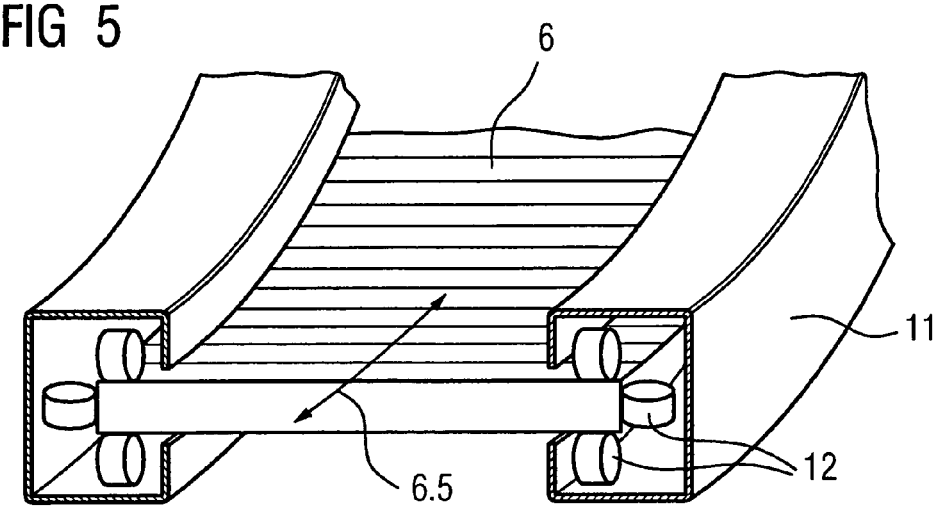
FIG. 5 is a perspective detail view of a moveable diaphragm with a guide mechanism in accordance with the invention.

FIG. 5 shows a perspective detail view of a movable diaphragm 6 with guide mechanism. The diaphragm 6 is held to the right and left by a C-shaped guide track 11. A number of bearing elements 12 are arranged within the guide track 11, preferably roller bearings that enable a friction-minimized movement with the diaphragm 6 along the direction 6.5.

Figure 6:
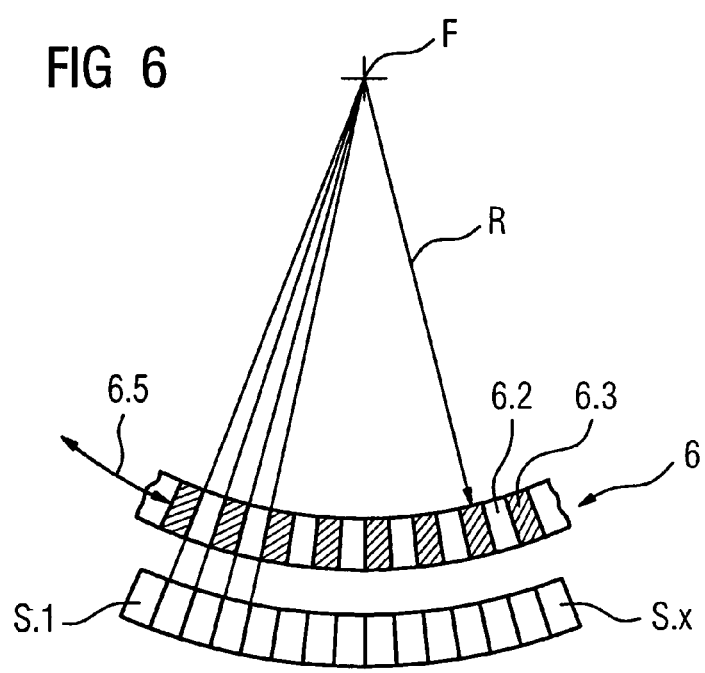
FIG. 6 is a lateral detail view of a section of a diaphragm that is positioned in front of individual detector elements in accordance with the invention.

In a side view, FIG. 6 shows a section of a diaphragm 6 that is positioned in front of individual detector elements S.1 through S.x, each of which has a scintillator element. The diaphragm 6 has a number of webs 6.3 and slots 6.2. The webs 6.3 should at least partially cover the individual detector elements S.1 through S.x, and thus reduce the aperture. In order to achieve a precise positioning of the webs 6.3 in front of the detector elements S.1 through S.x, for example, the drive motor 10 from FIG. 4 can be stopped at the desired positions via one or more limit switches.

Figure 7:
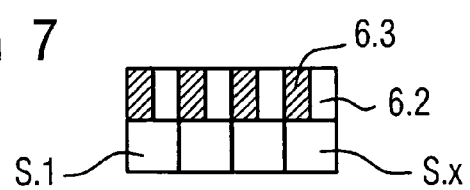
FIG. 7 is an enlarged section of the diaphragm of FIG. 6.

The exact positioning of the diaphragm 6 with its webs 6.3 and slots 6.2 in front of the individual detector elements S.1 through S.3 is explained in FIG. 7. The partial covering of areas of the individual detector elements S.1 through S.x is visible in FIG. 7. The left surface of each individual detector element S.1 through S.x is covered, and thus the impingement of x-rays is prevented. For simplicity, the detector diaphragm and the detector are shown in FIG. 7 without the existing curve.

In summary, the invention provides a computed tomography apparatus with a movable detector diaphragm that is arranged such that a reduction of the design depth of the gantry housing along the z-axis is achieved, while increasing the tilt angle of the gantry with regard to the z-axis (and thus with regard to the patient bed). Overall, a computer tomography apparatus can be executed very compact, primarily due to the reduction of the design depth.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising:
   a gantry having an x-ray tube and a radiation detector mounted thereon for rotation around a system axis, said radiation detector having a width disposed in a direction of the system axis and a length disposed substantially perpendicularly to said system axis and proceeding in a circumferential direction of said gantry said detector exhibiting a curvature along said circumferential direction;
   a diaphragm disposed in front of said radiation detector and having a movable diaphragm element, said movable diaphragm element having a curvature along said circumferential direction conforming to said curvature of said radiation detector; and
   a movement device connected to said diaphragm element to move said diaphragm element over said radiation detector along said circumferential direction to partially cover said radiation detector.

2. A computed tomography apparatus as claimed in claim 1 wherein said movement device comprises at least one guide track along which said diaphragm element is moved.

3. A computed tomography apparatus as claimed in claim 2 wherein said guide track comprises roller elements.

4. A computed tomography apparatus as claimed in claim 2 wherein said diaphragm element comprises roller elements.

5. A computed tomography apparatus as claimed in claim 1 wherein said movement device comprises at least one flexible pulling element connected to said movable diaphragm element.

6. A computed tomography apparatus as claimed in claim 5 wherein said flexible pulling element is selected from the group consisting of chains and cables.

7. A computed tomography apparatus as claimed in claim 1 wherein said movement device comprises at least one drive mechanism mechanically connected to said movable diaphragm element.

8. A computed tomography apparatus as claimed in claim 7 wherein said drive mechanism comprises a motor selected from the group consisting of electromechanical motors, hydraulic motors and pneumatic motors.

9. A computed tomography apparatus as claimed in claim 7 wherein said drive mechanism comprises an adjustment element.

10. A computed tomography apparatus as claimed in claim 7 wherein said drive mechanism comprises a motor and a plurality of switch elements for controlling said motor to position said diaphragm element in front of said radiation detector.

11. A computed tomography apparatus as claimed in claim 10 wherein said switch elements comprise limit switches.

12. A computed tomography apparatus as claimed in claim 1 wherein said radiation detector is a multi-row detector, and wherein said movable diaphragm element comprises a plurality of divisions respectively approximately corresponding to divisions of said multi-row radiation detector.

13. A computed tomography apparatus as claimed in claim 1 wherein said movable diaphragm element is flexible at least in said circumferential direction.

14. A computed tomography apparatus as claimed in claim 13 wherein said movable diaphragm element is comprised of a plurality of sub-elements.

15. A computed tomography apparatus as claimed in claim 14 wherein said sub-elements of said diaphragm element are connected to each other so as to be layered atop one another by said movement device.

16. A computed tomography apparatus as claimed in claim 14 wherein said sub-elements of said diaphragm element are connected to each other so as to be stacked in series by said movement device.

17. A computed tomography apparatus as claimed in claim 1 wherein said gantry comprises a storage space disposed inside said gantry proceeding along said circumferential direction in which said diaphragm element is stowed by said movement device when said diaphragm element is not in front of said radiation detector.

18. A computed tomography apparatus as claimed in claim 17 wherein said storage space is disposed immediately adjacent said radiation detector in said circumferential direction of said gantry.

19. A computed tomography apparatus as claimed in claim 1 wherein said curvature of said radiation detector has a constant radius of curvature.

* * * * *